US006935552B2

(12) United States Patent
Komai et al.

(10) Patent No.: US 6,935,552 B2
(45) Date of Patent: Aug. 30, 2005

(54) HIGH-PRECISION METHOD AND APPARATUS FOR EVALUATING CREEP DAMAGE

(75) Inventors: Nobuyoshi Komai, Nagasaki (JP); Fujimitsu Masuyama, Nagasaki (JP); Masahiro Kobayashi, Nagasaki (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 10/256,137

(22) Filed: Sep. 27, 2002

(65) Prior Publication Data

US 2003/0062397 A1 Apr. 3, 2003

(30) Foreign Application Priority Data

Sep. 28, 2001 (JP) ........................................ 2001-300988

(51) Int. Cl.$^7$ ................................................ B23K 31/12
(52) U.S. Cl. ............................ 228/103; 228/9; 228/104
(58) Field of Search ............................... 228/102, 103, 228/104, 8, 9

(56) References Cited

U.S. PATENT DOCUMENTS

| | | | |
|---|---|---|---|
| 4,287,417 A | | 9/1981 | Komatsu et al. |
| 4,426,718 A | | 1/1984 | Hayashi et al. |
| 5,573,172 A | * | 11/1996 | Gore |
| 5,651,493 A | * | 7/1997 | Bielick et al. |
| 6,589,369 B2 | * | 7/2003 | Yokoi et al. |
| 2002/0146162 A1 | * | 10/2002 | Ozaki et al. |
| 2002/0179193 A1 | * | 12/2002 | Yokoi et al. |
| 2003/0062397 A1 | * | 4/2003 | Komai et al. |

FOREIGN PATENT DOCUMENTS

| | | | |
|---|---|---|---|
| DE | 19950313 | | 4/2001 |
| EP | 1298431 A2 | * | 4/2003 |
| JP | 56029142 | | 3/1981 |
| JP | 57141556 | | 9/1982 |
| JP | 59060347 | | 4/1984 |
| JP | 03209162 | | 9/1991 |
| JP | 04055744 A | * | 2/1992 |
| JP | 09072897 A | * | 3/1997 |
| JP | 10123123 | | 5/1998 |
| JP | 10170503 | | 6/1998 |
| JP | 02000258306 A | * | 9/2000 |
| JP | WO 02/14835 A1 | * | 2/2002 |

OTHER PUBLICATIONS

Translation of JP–02000258306A.*

* cited by examiner

*Primary Examiner*—Kiley Stoner
(74) *Attorney, Agent, or Firm*—Wenderoth, Lind & Ponack, L.L.P.

(57) ABSTRACT

A high-precision method for evaluating creep damage of high tension heat resistant steel used in high temperature exposed apparatuses involves comparing particle size behavior varying with creep damage progress of crystal grains having a crystal orientation difference of about 2 degrees or more, preferably 3 degrees or more at an evaluated part on the basis of a working curve or a working map prepared in advance by looking for the relation of grain sizes to creep damage extent. A high-precision apparatus evaluates the creep damage of high tension heat resistant steel used in high temperature exposed apparatuses. A measuring device measures particle size variation behavior of crystal grains or sub grains having a crystal orientation difference of about 2 degrees or more with regard to a specimen at the evaluated part of high tension heat resistant steel and a working curve or a working map prepared in advance by looking for the relation of the grain sizes with respect to the creep damage extent (including creep damage rates) at every level of loaded stress. The creep damage extent is evaluated by comparing the grain size variation behavior measured by the measuring device with a working curve or a working map selected on the basis of loaded stress.

8 Claims, 10 Drawing Sheets

(A) Base material (a) STBA24
(creep test condition: 550°C × 110MPa)

| Suspend time (h) | Creep damage rate (t/tr) | Note |
|---|---|---|
| 0 | 0.00 | As received |
| 1000 | 0.10 | |
| 2000 | 0.19 | |
| 3000 | 0.29 | |
| 4000 | 0.39 | |
| 5000 | 0.48 | |
| 6000 | 0.58 | |
| 7000 | 0.68 | |
| 8000 | 0.77 | |
| 9000 | 0.87 | |
| 10357 | 1.00 | Rupture |

(b) Heat STBA28
(creep test condition: 600°C × 130MPa)

| Suspend time (h) | Creep damage rate (t/tr) | Note |
|---|---|---|
| 0 | 0.00 | As received |
| 2000 | 0.10 | |
| 4000 | 0.20 | |
| 6000 | 0.30 | |
| 8000 | 0.40 | |
| 10000 | 0.50 | |
| 12000 | 0.60 | |
| 14000 | 0.70 | |
| 16000 | 0.80 | |
| 18000 | 0.90 | |
| 19984 | 1.00 | Rupture |

(c) Heat SUSTP347H
(creep test condition: 650°C × 130MPa)

| Suspend time (h) | Creep damage rate (t/tr) | Note |
|---|---|---|
| 0 | 0.00 | As received |
| 2500 | 0.09 | |
| 5000 | 0.19 | |
| 7500 | 0.28 | |
| 10000 | 0.38 | |
| 12500 | 0.47 | |
| 15000 | 0.57 | |
| 17500 | 0.66 | |
| 20000 | 0.76 | |
| 22500 | 0.85 | |
| 26436 | 1.00 | Rupture |

(B) Welding joint (a) STBA24
(creep test condition: 550°C × 110MPa)

| Suspend time (h) | Creep damage rate (t/tr) | Note |
|---|---|---|
| 0 | 0.00 | As received |
| 1000 | 0.10 | |
| 2000 | 0.20 | |
| 3000 | 0.31 | |
| 4000 | 0.41 | |
| 5000 | 0.51 | |
| 6000 | 0.61 | |
| 7000 | 0.71 | |
| 8000 | 0.82 | |
| 9000 | 0.92 | |
| 9803 | 1.00 | Rupture |

(b) Heat STBA28
(creep test condition: 600°C × 130MPa)

| Suspend time (h) | Creep damage rate (t/tr) | Note |
|---|---|---|
| 0 | 0.00 | As received |
| 1500 | 0.10 | |
| 3000 | 0.19 | |
| 4500 | 0.29 | |
| 6000 | 0.39 | |
| 7500 | 0.48 | |
| 9000 | 0.58 | |
| 10500 | 0.67 | |
| 12000 | 0.77 | |
| 13500 | 0.87 | |
| 16568 | 1.00 | Rupture |

(c) Heat SUSTP347H
(creep test condition: 650°C × 130MPa)

| Suspend time (h) | Creep damage rate (t/tr) | Note |
|---|---|---|
| 0 | 0.00 | As received |
| 2500 | 0.10 | |
| 5000 | 0.20 | |
| 7500 | 0.30 | |
| 10000 | 0.41 | |
| 12500 | 0.51 | |
| 15000 | 0.61 | |
| 17500 | 0.71 | |
| 20000 | 0.81 | |
| 22500 | 0.91 | |
| 24687 | 1.00 | Rupture |

FIG. 9

| Creep damage rate | Crystal | Crystal orientation difference | Average grain size($\mu$m) | |
|---|---|---|---|---|
| 0 | A~D | 20° or more | 103 | |
| 0.3 | A1~D3 | 3° or more | 37 | 39 |
| | B1~B4 | 3° or more | 41 | |
| | C1~C4 | 3° or more | 39 | |
| | D1~D3 | 3° or more | 37 | |
| 0.9 | A1-1~A1-2~A2~A3-2 | 3° or more | 20 | 21 |
| | B1-1~B3~B4-3 | 3° or more | 18 | |
| | C1~C2-1~C4 | 3° or more | 23 | |
| | D1-1~D2-1~D3 | 3° or more | 19 | |

FIG. 10

| Creep damage rate | Crystal | Crystal orientation difference | Average grain size(μm) | |
|---|---|---|---|---|
| 0 | A1~B3 | 3° or more | 22 | 24 |
| | C1-1~D2 | 3° or more | 23 | |
| | E1-1~F2 | 3° or more | 24 | |
| | G1~H | 3° or more | 30 | |
| 0.5 | A~B | 3° or more | 51 | 39 |
| | C1~D2 | 3° or more | 31 | |
| | E1~F | 3° or more | 37 | |
| | G1~H | 3° or more | 42 | |
| 0.9 | A,B | 3° or more | 52 | 52 |
| | C,D | 3° or more | 60 | |
| | E,F | 3° or more | 58 | |
| | G1~H | 3° or more | 42 | |

HIGH-PRECISION METHOD AND APPARATUS FOR EVALUATING CREEP DAMAGE

BACKGROUND OF THE INVENTION

1. Field of the Invention

The present invention relates to a method and an apparatus for evaluating the extent of creep damage in high-tension heat resistant steel used in a power plant with precision and in a short period of time.

2. Description of the Related Art

Since thermal power plants in Japan had been constructed intensively for about ten years from 1955 to 1965, over half of the total plants have been operated for more than 100,000 hours. In order to operate the plants safely hereafter, a precise life evaluation is needed for proper maintenance. A destructive test has been hitherto used as the most reliable evaluation method. The problem was that the method consumed much time and cost in comparison to other methods. Recently, a more convenient method, such as a metallographical evaluation method, has been applied instead of the destructive test.

High-tension ferritic steel or austenite stainless steel is used in recent high-pressure steam power plants. The metallographical method has not been applied to these steels because structural change owning to creep damage is small. Hence, evaluation methods for creep damage, such as a method by a convenient hardness measurement, have been proposed.

For instance, the applicant of the present invention disclosed a method for evaluating the rest of the life of ferritic heat resistant steel in Japanese laid open patent publication P1990-248860A. The method comprises the steps of measuring a hardness of both the part influenced by welding heat and a base metal, preparing a working curve chart denoting the relation of creep damage extent of the parts influenced by welding heat with respect to the hardness differences between the parts influenced by welding heat and the base metal, and finding the creep damage extent by applying a hardness difference between the measuring part influenced by welding heat and the base metal to the working curve.

However, a problem of the accuracy of evaluating the creep damage by the above method still remains, because the hardness varies with factors such as the accuracy of the hardness measurement, heat treatment, and aging, besides creep damage.

SUMMARY OF THE INVENTION

In view of the prior problems, the present invention provides a method and an apparatus for evaluating precisely and in a short period of time the creep damage to the parts influenced by welding heat of base metal and a welded joint of heat resistant steel used in a high temperature exposed apparatuses of thermal power plants etc., specifically of such heat resistant steels as ferric steel based on two phase structure of ferritic and pearlite, high tension heat resistant ferritc steel based on a martensitic structure or austenitic stainless steel.

Recently, instruments and studies for metallographic analysis have advanced so that a microstructure change caused by creep damage in a high tension heat resistant steel that is beginning to be used in power plants can be analyzed.

A microstructure of a heat resistant steel consists essentially of old austenitic grains having a large crystal orientation difference between adjacent crystals and comparatively small subgrains together with the old austenitic grains. The sub grains have a crystal orientation difference of about 2 degrees or more or preferably 3 degrees or more between adjacent crystals. The inventor of the present invention found that a time-saving and precise creep damage evaluation can be performed by comparing the behavior of these crystal grains in increasing or decreasing in size on the basis of a working curve or a working map prepared in advance by looking for the relation of the grain sizes with respect to the creep damage extent. Hence, an aspect of the present invention is that creep damage can be evaluated by a change in an average grain size of crystal grains having a crystal orientation difference of about 2 degrees or more, preferably 3 degrees or more. To put it more simply, without distinguishing old austenitic grains from sub grains, a change of the smallest grain size measurement observed with a conventional instrument (e.g. EBSP) can evaluate creep damage by applying the observed grain size to a working curve.

More specifically, to evaluate creep damage of base metal, which is used in high temperature apparatuses, of ferritic steel and austenitic stainless steel having two phase structure of ferrite and pearlite, a part influenced by welding heat of ferritic heat resistant steel based on a tempered martensitic structure or a tempered bainite structure and having a fine grain region therein, or a part influenced by welding heat of austenitic stainless steel having a coarse grain region, crystal grains or sub grains having a crystal orientation difference of about 2 degrees or more, preferably 3 degrees or more at the evaluated part, are preferably compared in terms of particle size variation, more preferably average particle size behavior, which decreases with creep damage progress, on the basis of a working curve or a working map prepared in advance by looking for the relation of the grain sizes with respect to the creep damage extent.

To evaluate creep damage of a coarse grain region of a base metal of ferritic steel, a coarse grain region influenced by welding heat of ferritic heat resistant steel having a tempered martensitic structure or a tempered bainite structure or a coarse grain region influenced by welding heat of ferritic steel having two phase structure of ferrite andpearlite, crystal grains or sub grains having a crystal orientation difference of about 2 degrees or more, preferably 3 degrees or more at an evaluated part, are preferably compared in terms of particle size variation, more preferably average particle size behavior, which decreases with creep damage progress, on the basis of a working curve or a working map prepared in advance by looking for the relation of the grain sizes with respect to the creep damage extent.

Ordinary crystal grains, which mean old austenitic grains, are observed in all heat resistant steel. The grain cluster is referred to as a large obliquity grain cluster. The crystal orientation difference of the adjacent crystals is said to be approximately 20 degrees. The sub crystal grains are referred to as a region of a small obliquity grain cluster unlike with old austenitic grains. The crystal orientation difference of the adjacent crystals is as very small as 1–3 degrees. Therefore, the grain cluster is so unstable that the cluster is apt to migrate by creep strain. The sub crystal grains whose grain size is smaller than that of old austenitic grains exist in old austenitic grains. It is often the case that the sub crystal grains do not exist until heat treatment. There are many fine lath structures of rod shape surrounded by small obliquity grain clusters in material having a tempered martensitic structure or a tempered bainite structure. According to the present invention, since the lath structures are also surrounded by sub crystal grain clusters, an average grain size is determined by taking into account the lath structures to evaluate creep damage.

The relation between average grain size and creep damage extent is affected by stress, though the effect of temperature is small. It is preferable to find in advance the relation between creep damage rates corresponding to each stress loaded to a creep damage evaluation part and average grain size.

Figure 6A:
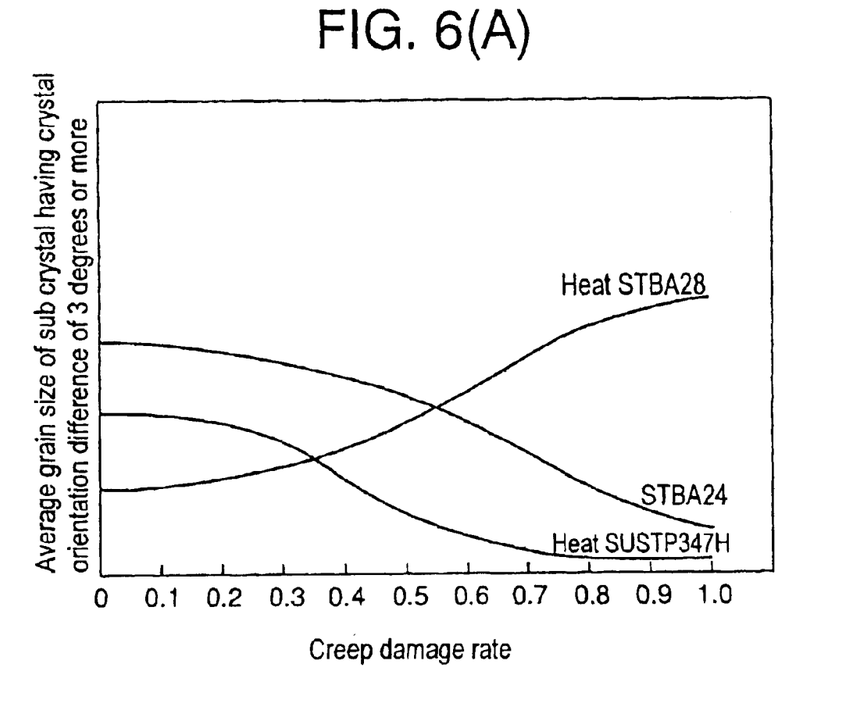
FIG. 6(A) is a graph chart showing a relation between grain size changes of sub grains and creep damage rates regarding base metal and FIG. 6(B) regards a joint welding part.
Figure 6B:
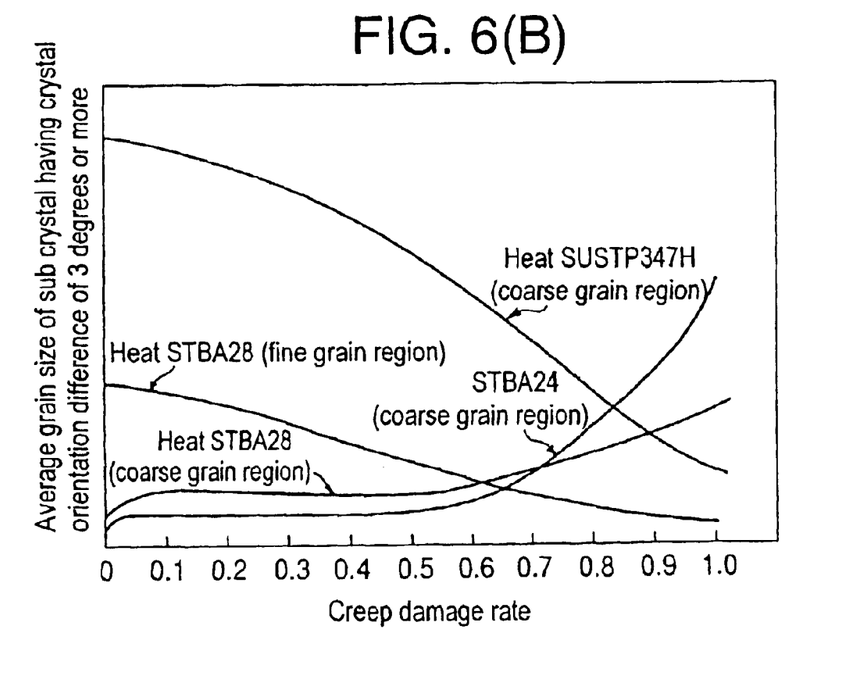

Therefore, a plurality of curved lines denoting the relation between creep damage rate and average grain size should be drawn at many levels of stress to formulate a series of maps, that is, a 3D map made by stacking a plurality of graphical drawings shown in FIG. 6 for a plurality levels of stress. In order to evaluate creep damage, a curved line in one of the drawings is preferably selected for the corresponding stress, or two curved lines in FIG. 6(A) and FIG. 6(B) are preferably interpolated to find a curved line of the corresponding stress.

Further according to the present invention, the map is substantially a set of working curves of creep damage extent vs. sub crystal grain size prepared for each prescribed stress. A curved line is selected from the working curves of the map or a curved line is made by interpolating two curved lines with regard to a loaded stress of an evaluated part. The creep damage of the part is found from the thus sought curved line.

Another aspect of the present invention relates to an apparatus for evaluating creep damage, with which the invention is effectively carried out. The apparatus comprises a measuring device for measuring particle size variation behavior of crystal grains or sub grains having a crystal orientation difference of about 2 degrees or more, preferably 3 degrees or more with regard to a specimen at an evaluated part of high tension heat resistant steel, and a working curve or a working map prepared in advance by looking for the relation of the grain sizes with respect to the creep damage extent (including creep damage rates) at every level of loaded stress. A creep damage extent is capably evaluated by comparing the grain size variation behavior measured by the measuring device with a working curve or a working map selected on the basis of a loaded stress.

In this case, it is preferable that, with the measuring device, an electron beam is irradiated on the specimen, from which a TEM-Kikuchi pattern appears due to the irradiation. The pattern is taken into a TV camera coated with phosphoric acid on its surface to observe and analyze it. The map is preferably a 3D map made by stacking a plurality of working curve charts denoting a relation of creep damage extent and average grain sizes for a plurality of prescribed levels of stress.

DETAILED DESCRIPTION OF PREFERRED EMBODIMENTS

The invention will now be described below in detail by way of example with reference to the accompanying drawings. It should be understood, however, that the description herein of specific embodiments such as to the dimensions, the kinds of material, the configurations and the relative disposition of the elemental parts is not intended to limit the invention to the particular forms disclosed. Rather, the intention is to disclose for the sake of example unless otherwise specifically described.

Now, in the following, the steps of creep damage evaluation according to the present invention are explained in the order of events.

First of all, a base metal of steel tubes of heat exchanging boilers for thermal power plant boilers were used for test specimens. More specifically, the materials are two kinds of ferritic steels and one kind of austenite stainless steel, details being described as follows.
1. Ferritic steel
1A. Ferritic steel based on two phase structure of ferrite and pearlite, JIS STBA24 *(2.25Cr—1Mo)φ50.8×t9.5 mm.
1B. High tension heat resistant ferritic steel based on a tempered martensitic structure, Heat STBA28 * (9Cr—1Mo—V—Nb)φ054.0×t10.2 mm
2. Austenite stainless steel Heat SUSTP347H * (18Cr—8Ni—Nb)φ45.0×t11.2 mm.

Figure 8:
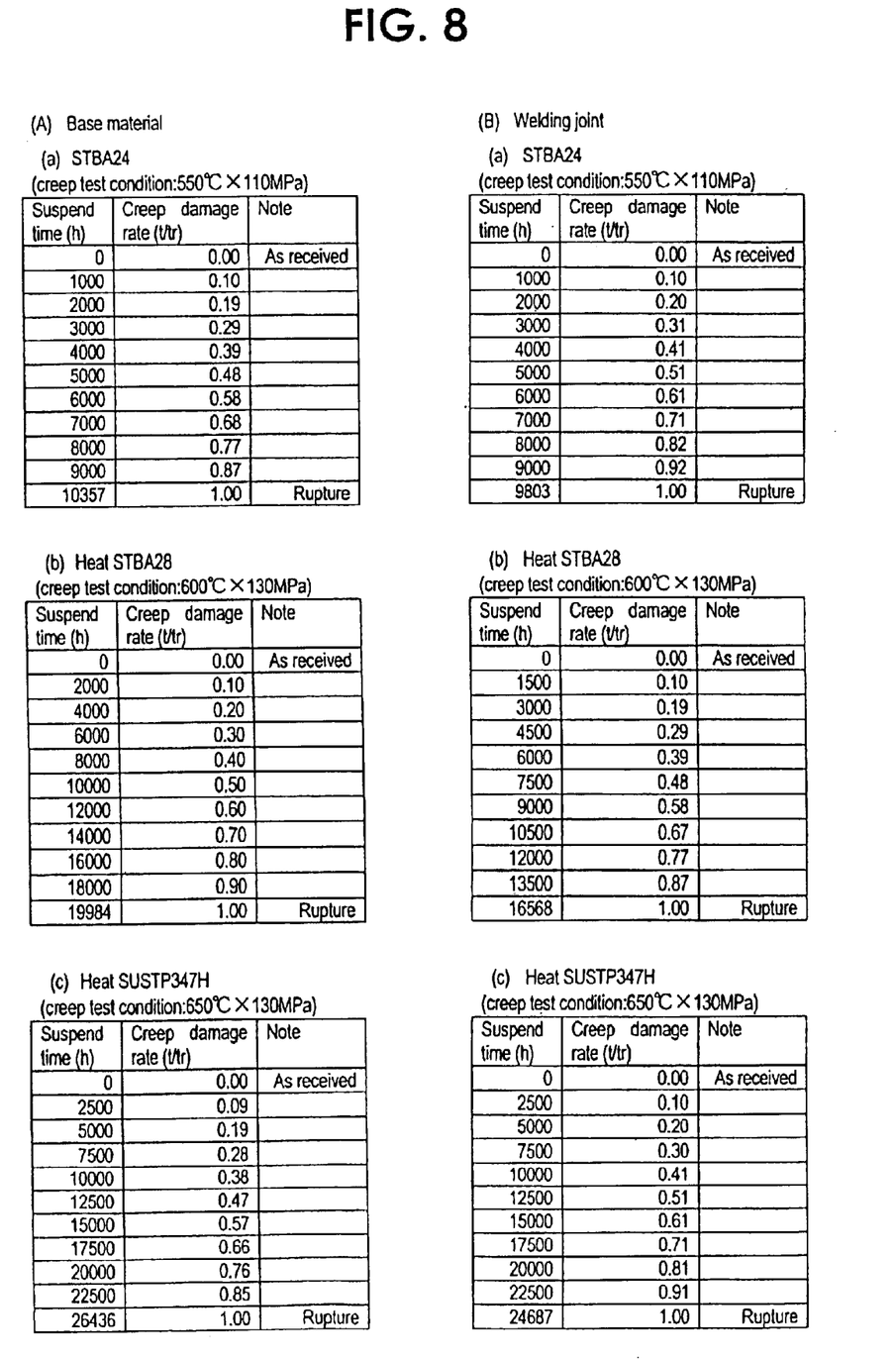
FIG. 8 includes tables showing creep damage rates of various test specimens.

Steel tubes of heat exchanging boilers set forth on FIG. 8 in "Construction of technical standard for hydraulic and thermal electrical apparatus" edited by former Agency of natural resources and energy.

Figure 1:
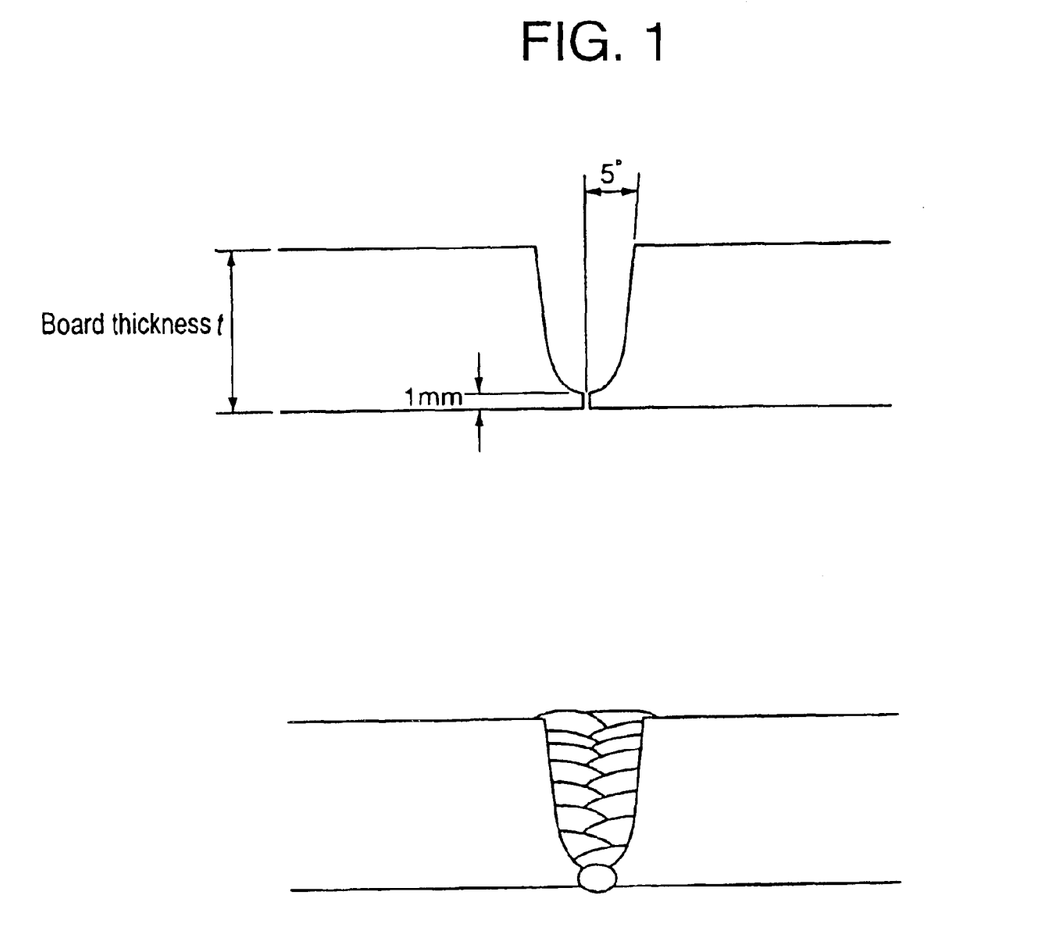
In FIG. 1, the upper drawing denotes a U groove form before welding and the lower drawing denotes a welding condition of a joint welding by multi layer laminate welding.

With regard to the above three kinds of base metal, joint welding with a U groove form shown in the upper part of FIG. 1 was carried out by multi layer laminate welding as shown in the lower part of FIG. 1 under the following condition.

Figure 2A:
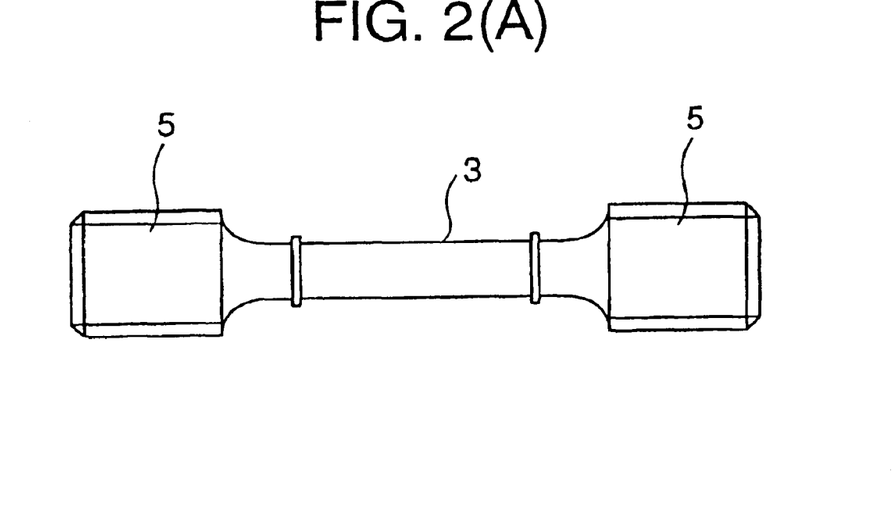
FIG. 2(A) and FIG. 2(B) show a test specimen form and a method for cutting the same from a welding part.
Figure 2B:
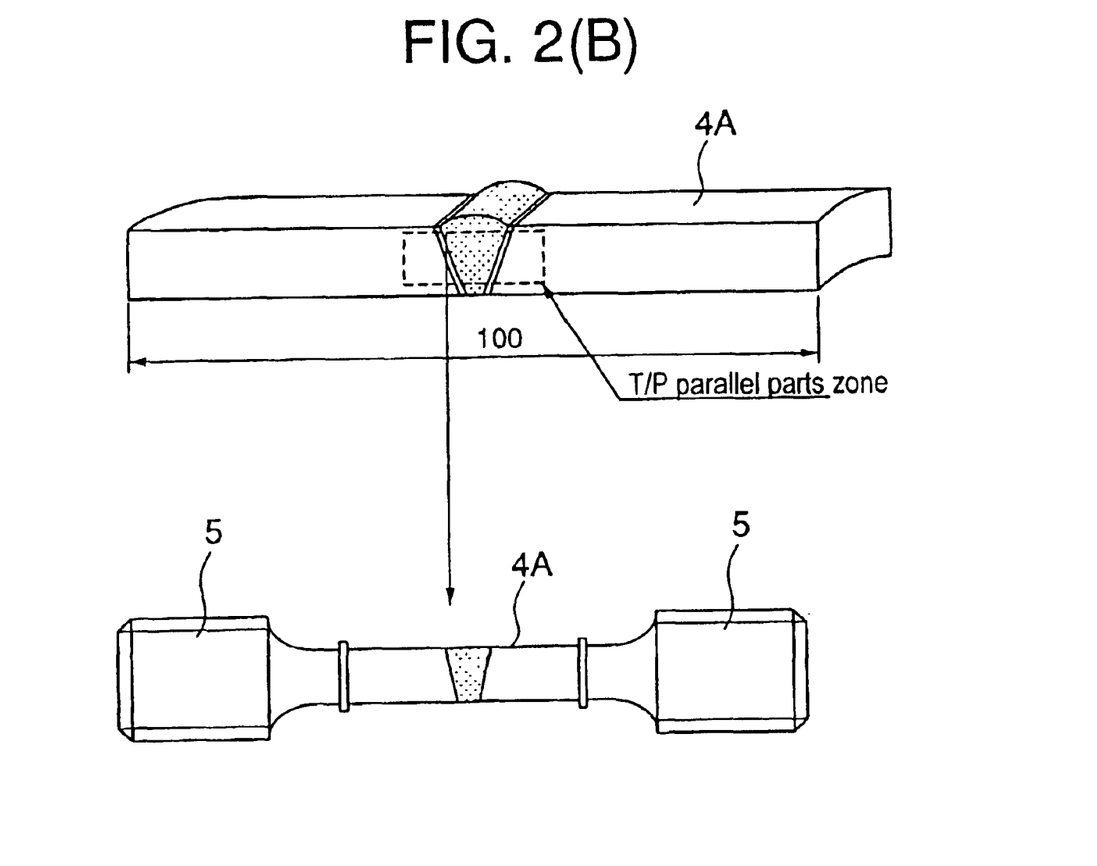

Welding method: TIG automatic welding
Welding wire: φ1.2 mm
Preheat: none
Welding voltage: 7–12 v
Welding current: 100–200 A
Heat treatment after welding: STB24 720° C.×0.5 h
  Heat STBA28 740° C.×0.5 h
  Heat SUSTP347H none Test specimens were taken from the three kinds of sample material of the base metal and welding joints. That is, creep test specimens shown in FIG. 2(A) and FIG. 2(B) were cut out from the base metal part and welding part, respectively, by a grind-cutting operation.

Creep testing was conducted under the following conditions:

550° C.×110 MPa for base metal and welding joints of 1A, STBA20;
600° C.×130 MPa for base metal and welding joints of 1B, Heat STBA28;
650° C.×130 MPa for base metal and welding joints of 2, heat SUSTP347H.

The between creep suspend time and creep damage rate is shown in FIG. 8.

A small piece was cut out from parallel part of a suspended creep test piece. The small piece was buried in resin in parallel with the direction of stress load, polished with until #1200 Emery paper and finally finished with 0.1 $\mu$m diamond paste to a mirror surface. The polished surface was electro polished in 10% perchloric acid/ethanol solution with an applied voltage of approximately 15 volts to remove the processed layer.

Figure 3:
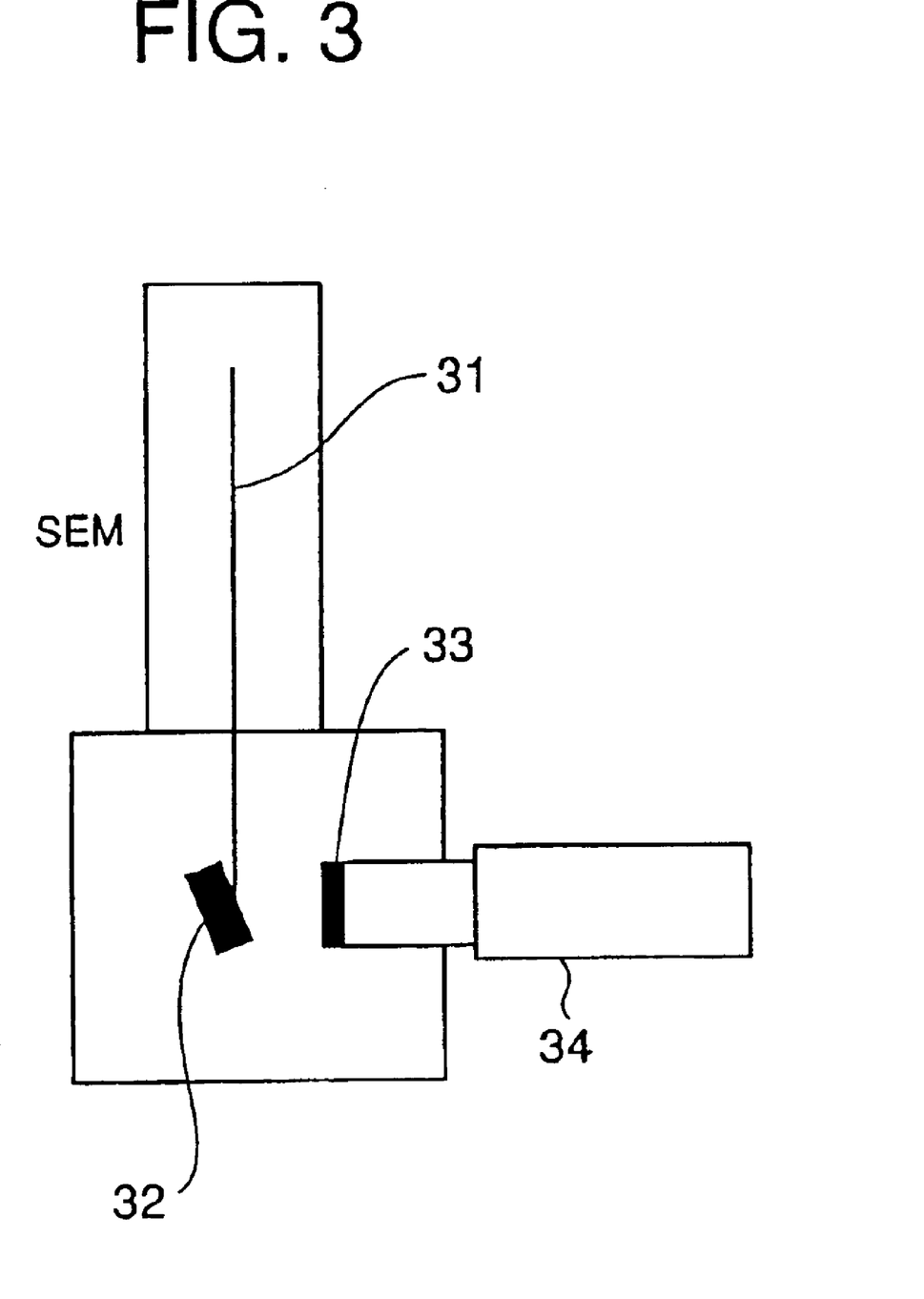
FIG. 3 shows an apparatus for observing and analyzing a crystal orientation pattern by known EBSP method.

Then, crystal orientation was analyzed with the test piece obtained above by a crystal orientation-analyzing instrument. Crystal orientation analyzing was made by a known EBDP (Electron Backscatter Diffraction Pattern) method. EBSP method has an accuracy of a spatial resolution of 0.1 $\mu$m, a measuring depth of 0.05 $\mu$m, an angle range of ±40°, and a bearing accuracy of 0.50°. The method has high spatial resolution in comparison to ECP (Electron Channeling Pattern) method, though spatial resolution and bearing accuracy are inferior to those of the TEM/Kikuchi line method. A SEM is shown in FIG. 3 where the TEM/Kikuchi pattern emitted from a specimen 32, whichis set obliquely at an angle of about 70 degrees and irradiated with electron beam 31, is observed and analyzed by taking the pattern into a TV camera 34, the surface of which is coated with phosphoric acid 33. Thus, the method has distinguishing characteristics such as facile preparation of specimens and overwhelmingly quick affixing of index numbers, because bulk specimens can be observed. An orientation angle difference of adjacent crystal grains or sub grains can be evaluated quantitatively.

An average grain size is estimated by regarding an interface having a crystal orientation difference of about 2 degrees or more, preferably 3 degrees or more in the crystal orientation images obtained by the SEM as a boundary. Fine crystals having a comparatively small orientation angle of adjacent crystals in a cluster of old austenite grains having a comparatively large orientation angle are herein referred to as sub crystal grains.

Figure 4:
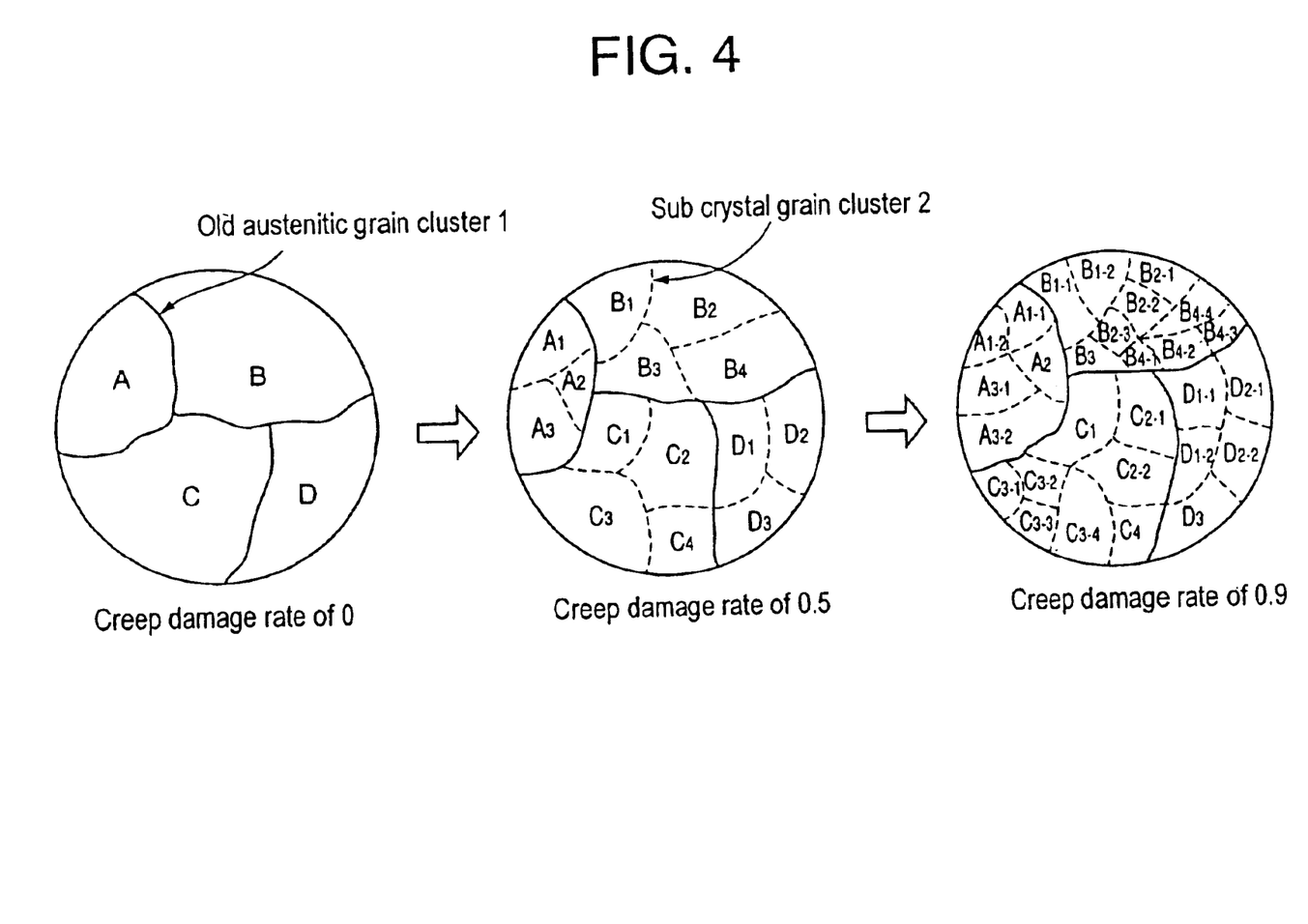
FIG. 4 includes pattern diagram showing a crystal structure change of crystal grains or sub grains accompanying creep damage with regard to base metal of STBA24 and heat SUSTP347H, a part influenced by welding heat of heat STBA28 (a fine grain region) and a part influenced by welding heat of SUSTP347H (a coarse grain region)
Figure 5:
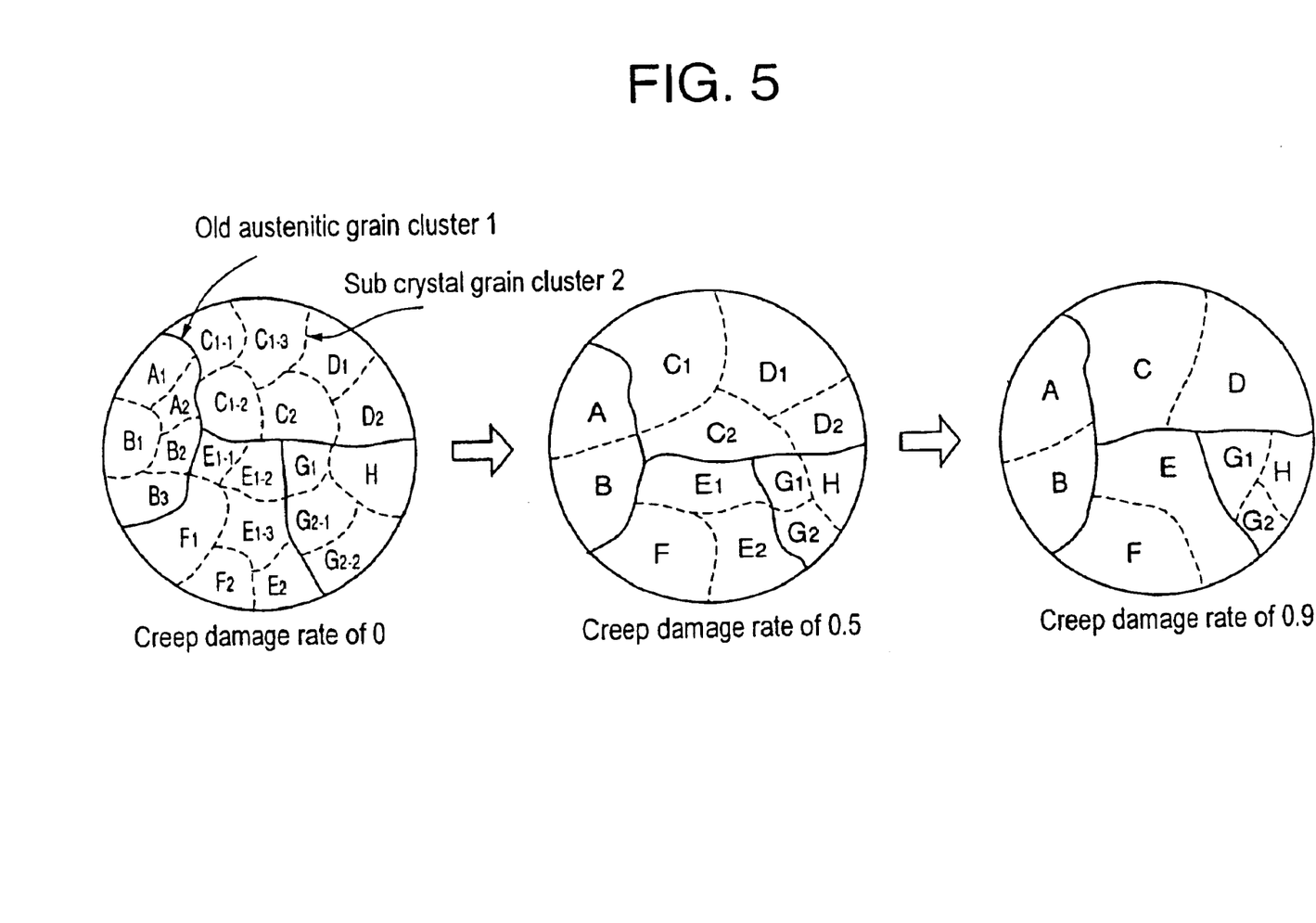
FIG. 5 includes pattern diagram showing a crystal grain change of a part influenced bywelding heat of STBA24 (a coarse grain region), and a crystal grain change of base metal and a part influenced by welding heat of heat STBA28 (a coarse grain region)

FIG. 4 and FIG. 5 are pattern diagrams showing structure changes of the sub crystal grains accompanied by creep damage. FIG. 4 includes pattern diagrams showing crystal changes of base metal of STBA24 and heat SUSTP347H, a part influenced by welding heat of heat STBA28 (a fine grain region), and a part influenced by welding heat of heat SUSTP347H (a coarse grain region). It can be seen that an average grain size becomes smaller as sub crystal grain clusters 2 are formed in an old austenite crystal grain cluster 1 with the increasing ratio of creep damages, 0→0.5→0.9.

FIG. 5 includes pattern diagrams showing crystal changes of a part influenced by welding heat of STBA24 (a coarse grain region), and base metal and a part influenced by welding heat of heat STBA28 (a coarse grain region). It can be seen that an average grain size becomes larger as sub crystal grain clusters 2 are decreased in an old austenite crystal grain cluster 1 with the increasing ratio of creep damages, 0→0.5→0.9.

Martensite and bainite lath, which have the same characteristics as a sub grain cluster, were also regarded as a sub grain.

Figure 9:
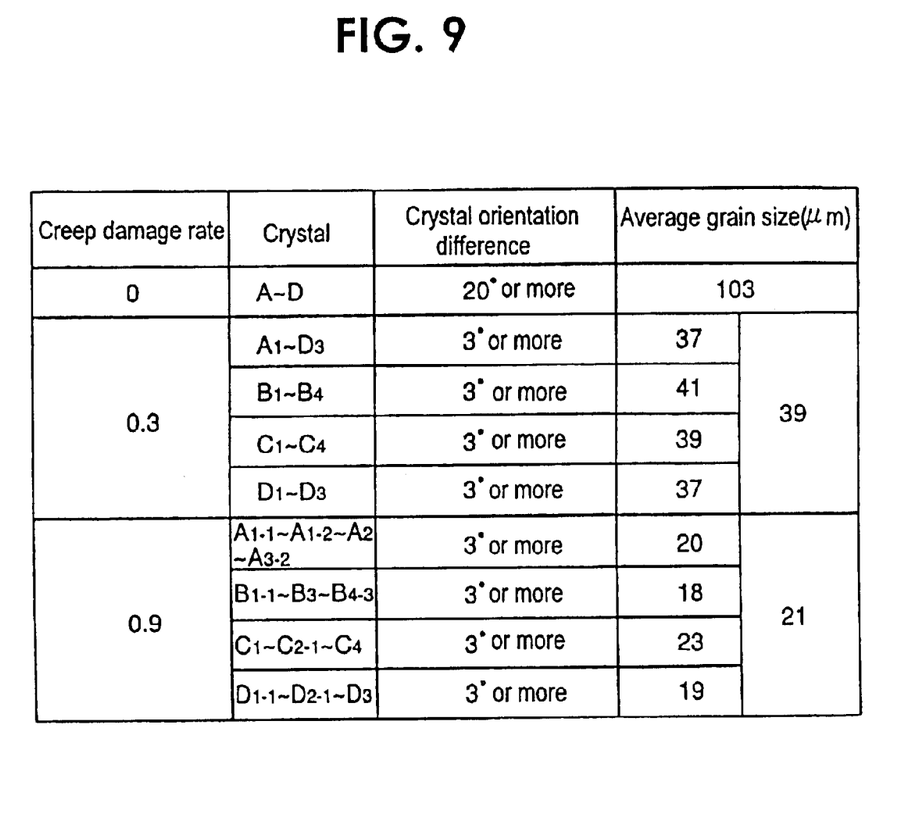
FIG. 9 is a table showing crystal orientation differences and average grain sizes in base material.
Figure 10:
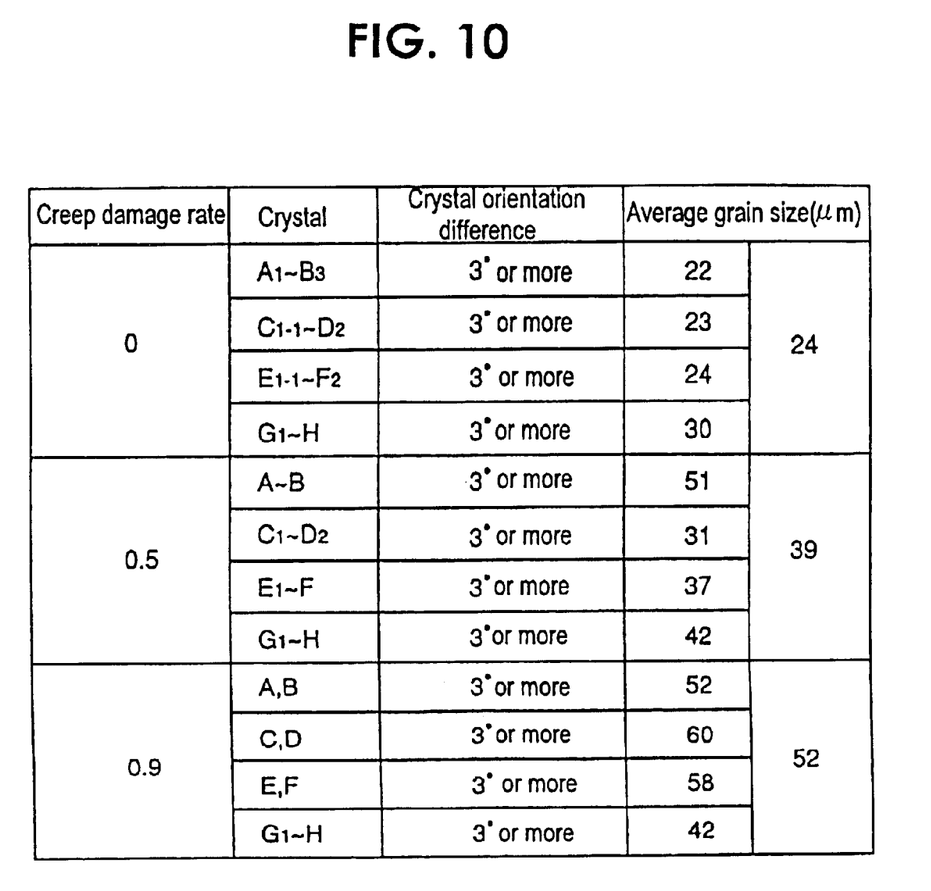
FIG. 10 is a table showing crystal orientation differences and average grain sizes in heat STBA28.

Measured data of crystal orientation differences and average grain sizes accompanied by creep damage are shown in FIGS. 9 and 10.

Crystal orientation differences and average grain sizes of adjacent crystals of old austenite grain cluster 1(A-D) and sub grain cluster 2($A_1$-$D_3$, $A_1$ 1-$D_3$) accompanied by creep damage in base metal(2.25Cr—1Mo) of STBA24 are shown in FIG. 9.

Crystal orientation differences and average grain sizes of adjacent crystals of old austenite grain cluster 1(A-H) and sub grain cluster 2 ($A_1$-$G_1$) accompanied by creep damage in heat STBA28 are shown in FIG. 10.

A sub grain cluster 2 is referred to as a grain cluster of small crystal orientation difference. On the other hand, an old austenite grain cluster is referred to as a large oblique angle grain cluster, generally of a big crystal orientation difference.

Reference signs used in FIGS. 9 and 10 correspond to those in FIGS. 4 and 5.

Behavior of grain size changes of sub grains in base material is different from that in a part influenced by welding heat, as shown in FIGS. 9 and 10. An average grain size of sub crystal grains behaves as shown in FIGS. 6 (A) and (B).

FIG. 6(A) illustrates that an average grain size becomes smaller as creep damage proceeds in base material of STBA24 and heat SUSTP347H, but, it becomes larger in base material of heat STBA28, which is denoted by the curve.

As for a welding joint part, FIG. 6(B) illustrates that an average grain size becomes larger as creep damage proceeds in a coarse grain region of a part influenced by welding heat of STBA24 and heat STBA28 and an average grain size turns finer in comparison to that before creep damage in a coarse grain region of a part influenced by welding heat of heat STBA28 and heat SUSTP347H.

Since stress has a significant effect on the relation of creep damage to average grain size, though testing temperature has little effect on it, it is preferable to find beforehand a relation of the creep damage rate to the stress applied to the part for evaluating creep damage to the average grain size.

The curves denoting the relation of creep damage rate to average grain size are preferably prepared for a plurality of levels of stress. Levels have a prescribed breadth therebetween and are integrated to a map, such as a 3D map, in which a plurality of graph charts shown in FIG. 6 for a plurality levels of stress are stacked.

Figure 7:
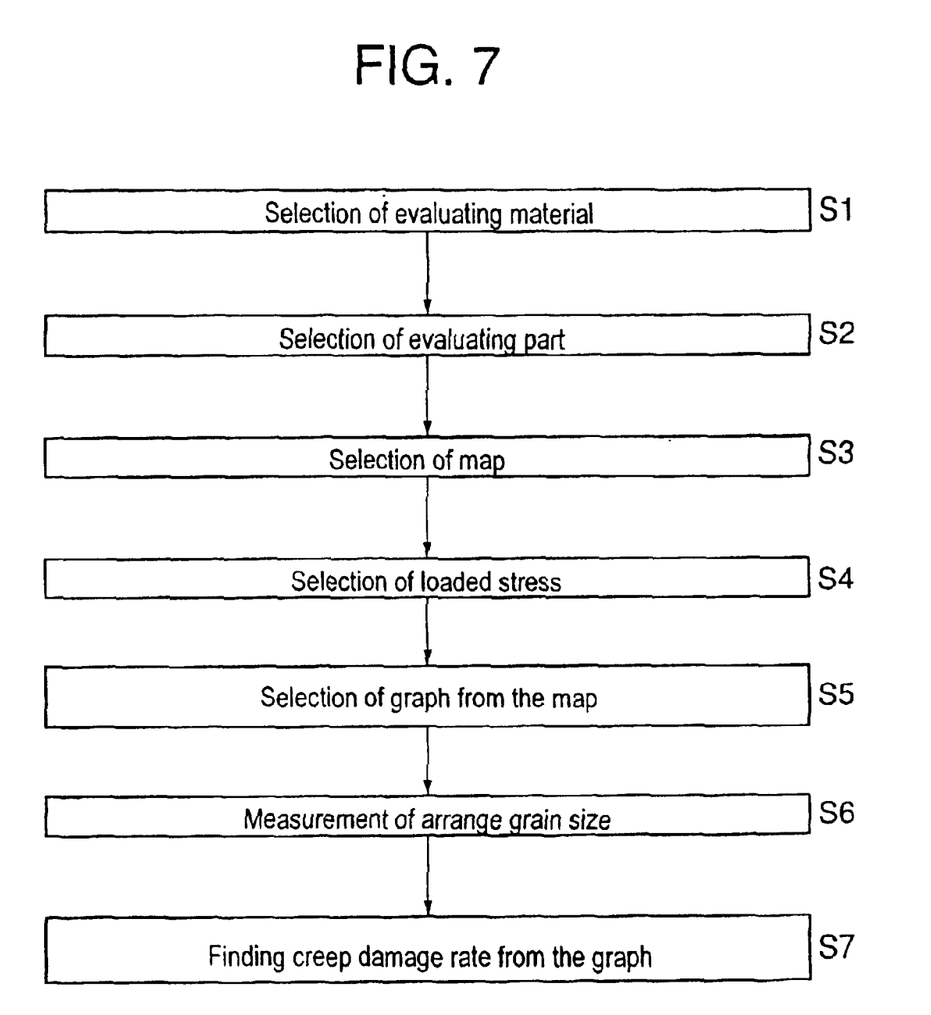
FIG. 7 is a flow chart showing the steps of finding a creep damage rate from the orientation difference and the grain size change of base metal and a part influenced by welding heat.

After preparation of the map, creep damage is evaluated by the following, referring to the flow chart shown in FIG. 7.

(S1) Selection of an evaluating material, for example, whether the material is STBA24, heat STBA28 or SUSTP347H or not.

(S2) Selection of an evaluated part, whether the part is base metal, a coarse grain region or a fine grain region of a part influenced by welding heat.

(S3) Selection of a map for the material and the evaluated part.

(S4) Selection of a loaded stress for the evaluated part.

(S5) Selection of a graph of a relation of an average grain size of crystal grains having a crystal orientation angle of about 2 degrees or more, preferably 3 degrees or more or sub crystal grains to creep damage rate corresponding to the evaluating stress, material and evaluated part from the selected map.

(S6) Measurement of an average grain size of crystal grains having an orientation angle of about 3 degree or more or of sub crystal grains of a test specimen with a crystal orientation-analyzing instrument using SEM.

(S7) A creep damage rate is found by applying the measured average grain size to the graph selected by step S5.

Thus, creep damage is precisely evaluated in a short period of time by measuring crystal or subcrystal grain size of test pieces collected from a plant apparatus using a graph of relation of creep damage rate to average grain size.

As explained above, according to the present invention a time consuming destructive test known to be a reliable evaluation method is not necessary, and creep damage evaluation having the same precision as the destructive test can be conducted over a very short period of time. Therefore, the life at a high-pressure part of a power plant subject to creep damage is precisely evaluated so as to estimate accurately the rest of the life of the power plant, which results in improving plant reliability.

What is claimed is:

1. A high-precision method for evaluating creep damage of base metal or a part influenced by welding heat of high tension heat resistant steel used in high temperature exposed apparatus, comprising comparing particle size behavior varying with progress of creep damage of any grains having a crystal orientation difference of 3 degrees or more at an evaluated part of the base metal of the part influenced by welding heat of high tension heat resistant steel, used in high temperature exposed apparatus, said comparing comprising determining a relation of grain sizes to creep damage extent on the basis of a working curve or a working map prepared in advance.

2. A high-precision method for evaluating creep damage of base metal, used in high temperature apparatus, of ferritic steel and austenitic steel having two phase structure of ferrite and pearlite, a part influenced by welding heat of ferritic heat resistant steel based on a tempered martensitic structure or a tempered bainite structure and having a fine grain region therein, or a part influenced by welding heat of austenitic stainless steel having a coarse grain region, comprising comparing particle size behavior varying with progress of creep damage of any grains having a crystal orientation difference of 3 degrees or more at an evaluated part of the base metal or the part influenced by welding heat, said comparing comprising determining a relation of grain sizes to creep damage extent on the basis of a working curve or a working map prepared in advance.

3. A high-precision method for evaluating creep damage of a coarse grain region of a base metal of ferritic steel a coarse grain region influenced by welding heat of ferritic heat resistant steel having a tempered martensitic structure or a tempered bainite structure or a coarse grain region influenced by welding heat of ferritic steel having two phase structure of ferrite or pearlite, comprising comparing particle size behavior varying with progress of creep damage of any grains having a crystal orientation difference of 3 degrees or more at an evaluated part, said comparing comprising determining a relation of grain sizes to creep damage extent on the basis of a working curve or a working map prepared in advance.

4. The high-precision method of claim 3, wherein said comparing particle size behavior comprises comparing average particle size behavior.

5. A high-precision method for evaluating creep damage of base metal or a part influenced by welding heat of high tension heat resistant steel used in high temperature exposed apparatus, comprising comparing particle size behavior varying with progress of creep damage of crystal grains having a crystal orientation difference of approximately 2 degrees or more or sub crystal grains at an evaluated part of the base metal of the part influenced by welding heat of high tension heat resistant steel, used in high temperature exposed apparatus, said comparing comprising determining a relation of grain sizes to creep damage extent on the basis of a working curve or a working map prepared in advance;

wherein said working map comprises a set of working curves of creep damage extent vs. crystal grains or sub crystal grain size prepared for each of a plurality of predetermined stresses, a curved line is selected from the working curves of the map or a curved line is made by interpolating two of the curved lines with regard to a loaded stress of the evaluated part, and creep damage of the evaluated part is found from the selected or made curved line.

6. A high-precision apparatus for evaluating creep damage of high tension heat resistant steel used in high temperature exposed apparatus, comprising:

a measuring means for measuring particle size variation behavior, in accordance with progress of creep damage, of crystal grains or sub grains having a crystal orientation difference of approximately two degrees or more with regard to a specimen of an evaluated part of the high tension heat resistant steel; and a working curve or a working map that has been prepared in advance by determining the relation of grain sizes with respect to extent of creep damage, including creep damage rates, at each of a plurality of stress loads;

wherein the extent of creep damage is evaluated by comparing grain size variation behavior, in accordance with the progress of creep damage, measured by said measuring means with a said working curve or a said working map on the basis of a stress load.

7. A high-precision apparatus for evaluating creep damage of high tension heat resistant steel used in high temperature exposed apparatus, comprising:

a measuring means for measuring particle size variation behavior, in accordance with progress of creep damage, of crystal grains or sub grains having a crystal orientation difference of approximately two degrees or more with regard to a specimen of an evaluated part of the high tension heat resistant steel; and a working curve or a working map that has been prepared in advance by determining the relation of grain sizes with respect to extent of creep damage, including creep damage rates, at each of a plurality of stress loads;

wherein the extent of creep damage is evaluated by comparing grain size variation behavior, in accordance with the progress of creep damage, measured by said measuring means with a said working curve or a said working map on the basis of a stress load; and wherein said measuring means irradiates an electron beam on the specimen at a predetermined angle to produce a TEM-Kikuchi pattern and comprises a TV camera coated with phosphoric acid on a surface thereof to receive the pattern so as to be able to observe and analyze the pattern.

8. A high-precision apparatus for evaluating creep damage of high tension heat resistant steel used in high temperature exposed apparatus, comprising:

a measuring means for measuring particle size variation behavior, in accordance with progress of creep damage, of crystal grains or sub grains having a crystal orientation difference of approximately two degrees or more with regard to a specimen of an evaluated part of the high tension heat resistant steel; and a working curve or a working map that has been prepared in advance by determining the relation of grain size with respect to extent of creep damage, including creep damage rates, at each of a plurality of stress loads;

wherein the extent creep damage is evaluated by comparing grain size variation behavior, in accordance with the progress of creep damage, measured by said measuring means with a said working curve or a said working map on the basis of a stress load; and wherein said working map comprises a 3D map made by stacking a plurality of working curve charts denoting a relation of progress of creep damage to average grain sizes for a plurality of levels of stress.

* * * * *